United States Patent [19]
Barrett

[11] 4,243,035
[45] Jan. 6, 1981

[54] SYRINGE WITH INTEGRAL SWAB

[76] Inventor: Howard G. Barrett, 1215 Briercliff Dr., Orlando, Fla. 32806

[21] Appl. No.: 49,129

[22] Filed: Jun. 18, 1979

[51] Int. Cl.³ ............................................... A61M 5/00
[52] U.S. Cl. .................................. 128/215; 128/218 R
[58] Field of Search .................. 128/215, 216, 218 R, 128/220, 221, 269; 206/15.3, 229, 364, 438

[56] References Cited

U.S. PATENT DOCUMENTS

| 2,090,354 | 8/1937 | Massman | 128/269 |
| 2,627,269 | 2/1953 | McGregor | 128/215 |
| 2,851,036 | 9/1958 | Lipari | 128/218 R |
| 3,270,743 | 9/1966 | Gingras | 128/215 |
| 3,680,559 | 8/1972 | Gorbahn | 128/220 |

Primary Examiner—John D. Yasko
Attorney, Agent, or Firm—Julian C. Renfro

[57] ABSTRACT

A novel hypodermic syringe and integral antiseptic dispenser, with the syringe having a barrel portion adapted to contain fluid to be injected. A needle is operatively mounted on one end of the barrel portion, and a plunger is located on the other end of the barrel portion, with appropriate manipulation of the plunger bringing about the injection of fluid from the needle. The improvement comprises a presoaked antiseptic dispenser that may be disposed on the barrel portion, with the antiseptic dispenser making it convenient to clean the intended injection site immediately before the injection. The antiseptic dispenser may take the form of a pad carried by the barrel portion of the syringe, or a generally cylindrical pad-carrying member encircling a portion of the needle end of the syringe, or any of a number of related configurations.

4 Claims, 14 Drawing Figures

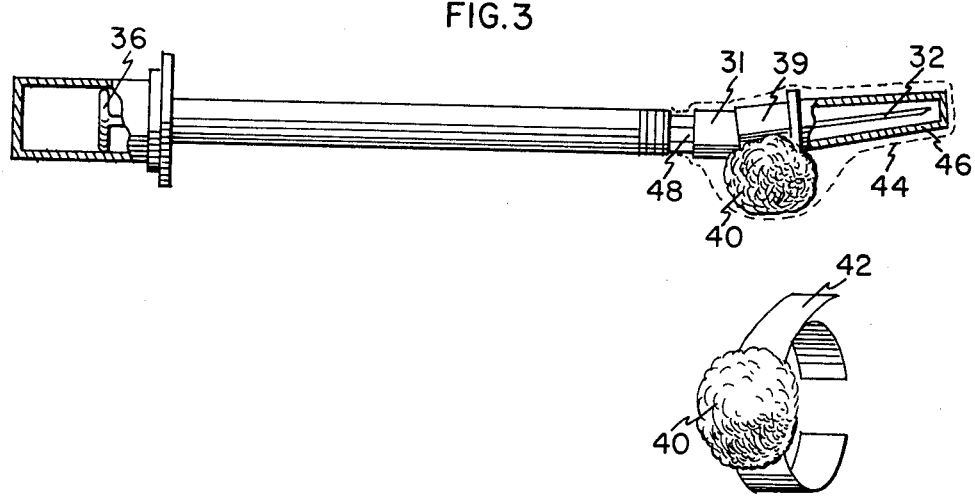
FIG.3
FIG.3a
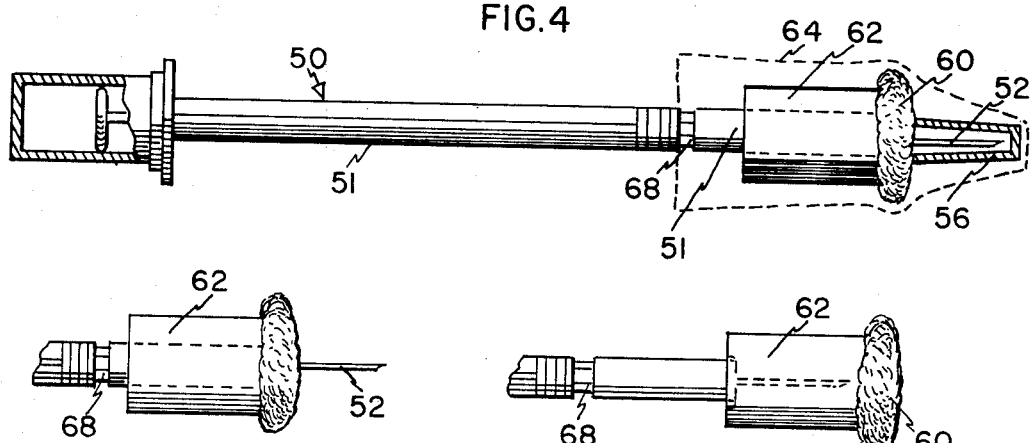
FIG.4
FIG.4a FIG.4b

SYRINGE WITH INTEGRAL SWAB

BACKGROUND OF THE INVENTION

In the past, when an injection was to be given, it was common to swab the affected area both before and after the injection. This is usually done by another than the one making injections, or by the injector laying the hypodermic syringe aside while the antiseptic is being applied with swab held in an entirely separate instrument. The need to lay aside the hypodermic syringe and use a separate instrument such as forceps or the like to apply the antiseptic to the point of injection caused considerably lost time.

When using the hypodermic syringes presently on the market, the physician still has to carry with him when visiting his patients, a bottle of antiseptic liquid such as ether, alcohol or the like as well as a box of absorbent material such as cotton. Furthermore, every time an injection has to be made, he has to go through several motions in order to sterilize the skin through which the injection is to be made. All these operations are time consuming and this is rather important, particularly for the physician whose schedule is usually very heavy. Also, it may happen from time to time that the physician runs out of either the antiseptic liquid or the absorbent cotton or both, and on such occasions none may be available on site. It was to overcome these and other disadvantages that the present invention was evolved.

SUMMARY OF THE INVENTION

I have invented a particularly convenient dispenser for antiseptics, which dispenser is capable of being secured to a hypodermic syringe so that a manipulation of the syringe will place the antiseptic on the point of injection before and after the injection, and make it possible to easily use the hypodermic syringe as the handle for the antiseptic dispenser.

The need to lay aside the hypodermic syringe and use a separate instrument such as forceps or the like to apply the antiseptic to the point of injection caused considerable lost time and inconvenience, and I have circumvented that problem by providing an antiseptic dispenser that is conveniently capable of being mounted directly on the hypodermic syringe itself.

The invention is particularly adaptable to the type of injection syringes now found on the market and which are of such low manufacturing cost that they may be discarded after use. In such syringes, both the cylinder and the piston thereof are made of plastic material which can easily be molded at very low cost. This type of injection syringe is extremely useful and possesses many advantages, one of which is certainly its low cost which makes it possible to discard it after use thus avoiding the necessity of cleaning and sterilizing. It is an object of this invention to still improve the usefulness of the known syringe of this type.

I have herein provided a number of embodiments of the basic idea of equipping an otherwise conventional hypodermic syringe with an integral antiseptic dispenser, making it conveniently possible to swab the injection site just before and just after an injection. This has been accomplished in a most convenient and inexpensive manner, as will be explained in detail hereinafter.

It is therefore the principal object of my invention to provide a hypodermic syringe and antiseptic dispenser combined in one unit whereby the time factor in making injections is greatly reduced as compared to conventional, present day techniques.

It is a further object of my invention to provide a tool for making antiseptic hypodermic injections that is durable in use and economical to manufacture.

It is another object of my invention to provide a hypodermic syringe complete in itself, which includes the necessary antiseptic in an evaporation-proof envelope attached to the syringe.

A further object of the invention resides in the provision of a protective assembly for the needle of a hypodermic injection syringe, which also includes a reserve of absorbent material and antiseptic liquid.

Still another object of the invention consists in providing a disposable syringe which is timesaving for the physician who has to use it and which can be manufactured at a relatively low cost on account of its simplicity and of the materials from which it can be made.

These and other objects, features and advantages will become more apparent as the description proceeds.

BRIEF DESCRIPTION OF THE DRAWINGS

FIG. 3 is a side elevational view of another embodiment of this invention, in this instance involving a pad rather than a toroidally shaped antiseptic dispenser, with the needle in this embodiment preferably slanted away from alignment with the centerline of the syringe;

FIG. 3a is a fragmentary perspective view to a larger scale of the pad used in connection with the embodiment of FIG. 3;

FIG. 4 is a side elevational view of an embodiment in which the antiseptic dispenser is carried on a generally cylindrical member designed to encircle a portion of the needle end of the barrel of the syringe;

FIGS. 4a and 4b are fragmentary views revealing various positions to which the generally cylindrical pad-carrying member of FIG. 4 can easily be moved;

DETAILED DESCRIPTION

Figure 1:
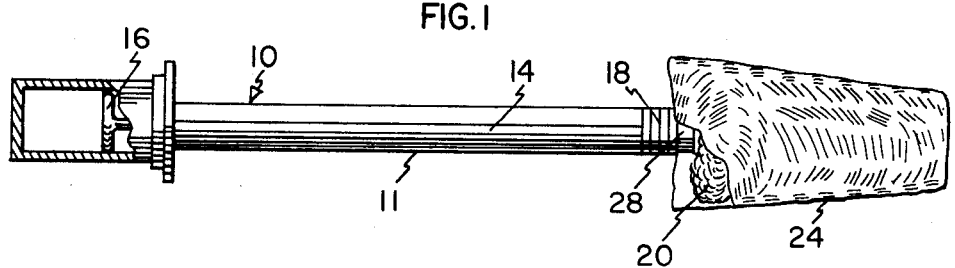
FIG. 1 is a side elevational view of a novel hypodermic syringe and integral antiseptic dispenser in accordance with this invention, showing a tear-away envelope employed over the needle end of the barrel, utilized to prevent evaporation of the antiseptic.
Figure 2:
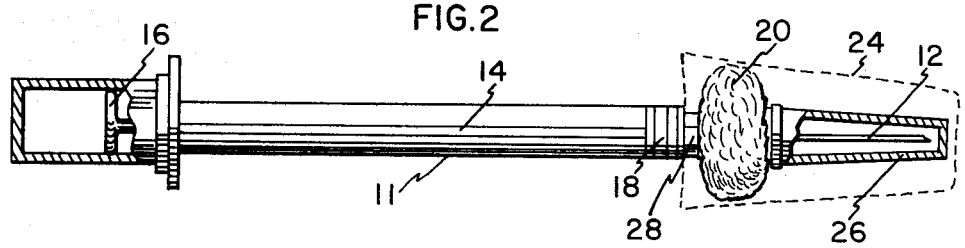
FIG. 2 is a side elevational view similar to FIG. 1 but showing the evaporation-preventing envelope removed to reveal the details of a first embodiment of an antiseptic dispenser.

Turning to FIGS. 1 and 2, it will there be seen that I have shown a first embodiment of a hypodermic syringe 10, which involves a barrel 11 equipped with a conventional needle 12, as best seen in FIG. 2. It is also equipped with a plunger 14 whose end 16 remote from the needle is configured to be engaged by the thumb of the user. As is conventional, a piston-like member 18 is disposed on the end of the plunger nearest the needle, with the piston-like member being arranged to engage the inner wall of the syringe barrel 11 in a leakproof manner as an injection, such as insulin, is administered.

It is the purpose of this invention to provide the user a convenient means for swabbing the skin area destined to receive the injection, and to that end I dispose a novel antiseptic dispenser 20 adjacent the needle end of the syringe in this first embodiment. As perhaps best seen in FIGS. 2 and 2a, the antiseptic dispenser in this embodiment takes the form of an encircling member such as of cotton or the like that is substantially donut shaped; note FIG. 2a. Although this pad could be provided dry by the manufacturer and then soaked with antiseptic immediately prior to the injection, in accordance with the preferred embodiment of this invention, the antiseptic dispenser or pad is presoaked, such as with isopropyl (rubbing) alcohol or the like.

In order to prevent a volatile antiseptic from evaporating, I provide as shown in FIGS. 1 and 2, an envelope-like member 24 such as of foil over the needle end of the device, with this of course being installed at the factory. Then, when the swabbing and thereafter the injection are to be performed, it is but a simple matter to remove the foil, which of course exposes the needle. Actually, I prefer to utilize a needle guard 26 over the needle as shown in FIG. 2, which prevents the foil from being torn by the needle during the handling procedure, and also prevents the needle from becoming bent during shipping.

Figure 1A:
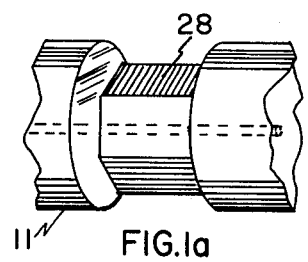
FIG. 1a is a fragmentary perspective view of a necked down portion of the barrel, this being utilized as an aid to obtaining an airtight seal of the envelope to the barrel.

Inasmuch as the foil 24 must fit tightly around the barrel in order to prevent evaporation of the antiseptic, I prefer to configure the barrel of the syringe to have a necked down portion 28 near the needle end of the syringe; note FIG. 1a that the necked down portion may have say six sides, although it of course could be circular and of a smaller diameter than the outer diameter of the syringe barrel. The foil portion contacting the barrel of the syringe is designed to coincide with the minimum cross section portion, as shown in FIG. 1, and has an airtight relation therewith.

Turning to FIG. 2, it will be noted that I have used like numbers to refer to components relatable to FIG. 1. In FIG. 2, the outline of the preferred embodiment of the foil member is shown in dashed lines, although it can be somewhat larger or somewhat smaller than this if desired.

Figure 2A:
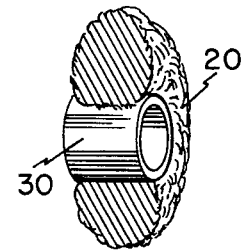
FIG. 2a is a fragmentary perspective view to a larger scale of the first embodiment of the antiseptic dispenser.

It will be observed from the embodiment of the antiseptic dispenser 20 shown in FIG. 2a, that the radially inner portion of this device may take the form of a portion 30 of a paper tube. In other words, the manufacture of this member may be accomplished by applying cotton along one side of a strip of cardboard, plastic or the like, which strip is then formed into a circle whose inner diameter enables it to fit snugly over the end of the syringe in the manner shown in FIG. 2.

As to the utilization of the device shown in FIGS. 1 and 2, at the time the syringe is to be used, the user tears off the foil covering from the needle portion of the device and then removes the needleguard 26. He or she then proceeds to fill the syringe, typically by inserting the needle through the rubber stopper of the bottle containing the drug to be injected.

Using the swab, which of course contains antiseptic applied at the factory, the user then proceeds to cleanse the skin area at the location where the injection is to be made. In this regard, it is most important to note that this swabbing procedure can be handled very easily by the ordinary person using only his or her two hands, and as previously explained, it is not necessary to set the syringe down in order that the swabbing can be accomplished, which of course made the procedure in accordance with prior art techniques very burdensome.

After the swabbing had been completed, the injection is given. Then the needleguard is replaced and using the pad, the injected area is swabbed again in order to clean up the injected area of dosage or blood. If the syringe is of the throw away type, it may now of course be discarded.

Turning to FIG. 3, it will be noted that I am not to be limited to a device having an antiseptic dispenser in the form of an encircling member of cotton. Rather, and as shown in FIG. 3, the antiseptic dispenser can take the form of a pad 40 that is non-symmetrically placed on the barrel 39 of the syringe. FIG. 3a shows, by way of example, a pad of cotton or the like mounted upon an encircling strip 42 of cardboard or plastic, and if desired, the end of the syringe in this embodiment may be configured such that the needle 32 is not disposed on the longitudinal centerline of the syringe body 31. Rather, in accordance with this embodiment, the needle 32 is angled away from the location of the pad 40 in order to afford plenty of access during the swabbing procedure.

As in the case of the proceeding embodiment, a foil covering 44 or the like is applied over the presoaked swab member 40 and the needle guard 46 in an airtight manner at the factory, which foil is removed just before the syringe is to be filled, and the swabbing and injection accomplished. As before, I may configure the syringe barrel to have a necked down portion 48 so as to enhance the likelihood of the foil member fitting in an air tight manner around the barrel 31 of the syringe.

Turning to FIG. 4, it will be noted that I have shown an embodiment wherein the swabbing device 60 is disposed on the end of a piston-shaped enclosure 62 that normally serves to encapsulate the needle end of the syringe 50. As before, I utilize an envelope member 64 applied at the factory to cover the presoaked swabbing material, needle 52 and needleguard 56, with a necked down location 68 preferably being used on the syringe barrel 51 in order to enhance the chances of the foil material fitting around the barrel in an air tight manner.

The piston shaped member 62 is typically of cardboard or plastic bent in a tubular form, with the end of such member being constructed of swabbing material 60 such as of cotton. As depicted in FIGS. 4 and 4a, the needle 52 normally protrudes through the swabbing material so that at such time as the foil and the needleguard have been removed, the user can proceed to fill the syringe by inserting the needle into the rubber stopper of the dispensing bottle.

After the syringe has been filled to the desired level, the user then moves the tubular member 62 to the position shown in FIG. 4b, so that the swabbing procedure can commence. It is to be noted that the swabbing can be conducted either with the tubular member in place on the syringe, or else the user can entirely remove the tubular member 62 and then proceed to carry on the procedure of cleansing the area to be injected. After the injection has been accomplished, the entire syringe assembly is ordinarily discarded after the affected area has been re-swabbed.

Figure 5:
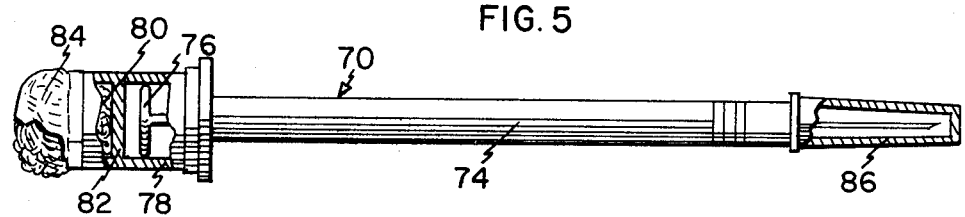
FIG. 5 is a side elevational view of an embodiment in which the integral antiseptic dispenser is utilized on the plunger end rather than the needle end of the syringe.
Figure 5A:
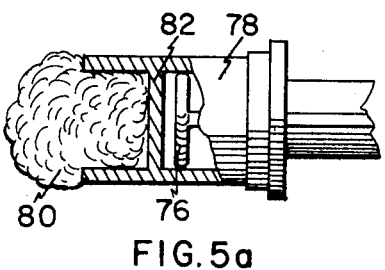
FIG. 5a is a view to a somewhat larger scale revealing other details of the antiseptic dispenser of FIG. 5.

Turning to FIG. 5, it will there be noted that I have provided an embodiment in which the syringe 70 is equipped with a plunger 74 whose thumb button 76 is equipped with an encompassing member 78 equipped with a pad 80 of swabbing material. The encompassing member 78 is generally cylindrical, and is equipped with a wall 82 at its mid portion as shown in FIG. 5a in order that the swabbing material 80 will not move out of the desired position in which it extends somewhat beyond the cylindrical sides of the member 78.

As before, the swabbing material is preferably presoaked at the factory with a suitable antiseptic, with evaporation being prevented by an envelope-like member 84 applied around the thumb button end of the device, which envelope is of course to be torn away at such time as the swabbing procedure is to commence.

Because of the convenient placement of the presoaked swabbing material on the end of the syringe remote from the needle, it is but a simple matter to effect a cleansing of the area to be injected, without being necessary to set down the syringe as it was previously necessary to do. The filling of the syringe and the utilization thereof may of course commence as soon as the needle guard 86 and the member 78 have been removed from the syringe.

Figure 6:
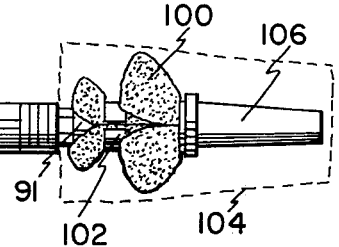
FIG. 6 is a side elevational view of an embodiment in which the antiseptic dispenser takes the form of a pad folded around the needle end of the barrel and held in place by a clip.
Figure 6A:
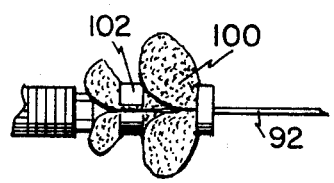
FIGS. 6a and 6b are fragmentary views revealing other details associated with the embodiment of FIG. 6.
Figure 6B:
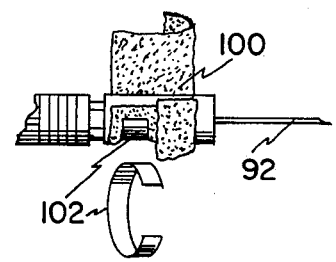

Turning to FIG. 6, it will be noted that I have there shown an embodiment in which the end of barrel 91 nearest the needle 92 is overwrapped with swabbing material in the form of a generally flat pad 100 that has been folded prior to being wrapped around the syringe body. The swabbing material 100 may be held in place in a number of ways, but I prefer to use a clip 102 such as of metal or plastic.

The swabbing material is preferably presoaked with a suitable antiseptic, and this portion of the device, including the needle 92 and the needle guard 106 are encapsulated by a suitable envelope 104 of foil or the like. As before, when the foil envelope has been torn away, the needle guard may be removed and the syringe filled. Thereafter, the area to be injected is cleaned with the swabbing material and the injection given.

Usually the clip 102 may be removed from the swabbing material in a fairly easy manner, so that the swabbing material may be used as a compress. It is to be noted that the swabbing material 100 may optionally be separated from a syringe body prior to the injection, rather than being used for cleaning the injection site while affixed to the barrel.

I claim:

1. A hypodermic syringe and integral antiseptic dispenser, said syringe having a barrel portion adapted to contain fluid to be injected, a needle operatively mounted on one end of said barrel, and a plunger located on the other end of said barrel portion, with manipulation of said plunger bringing about the injection of fluid from said needle, the improvement comprising a presoaked antiseptic dispenser disposed on said barrel portion, said antiseptic dispenser making it convenient to clean the intended injection site immediately before the injection, said antiseptic dispenser taking the form of a pad encircling the barrel portion of the syringe.

2. The syringe and antiseptic dispenser as defined in claim 1 in which an airtight, evaporation-inhibiting envelope is provided over the portion of the syringe containing said antiseptic dispenser, said envelope being relatively easily torn away at a time just before said antiseptic dispenser is to be used.

3. The syringe and antiseptic dispenser as defined in claim 2 in which said envelope is installed over the needle end of said barrel portion.

4. The syringe and antiseptic dispenser as defined in claim 2 in which said barrel portion is necked down at a location contacted by said envelope, thus to facilitate sealing said envelope around the barrel portion in an airtight manner.

* * * * *